United States Patent
Majeed et al.

(10) Patent No.: US 10,945,969 B2
(45) Date of Patent: *Mar. 16, 2021

(54) COMPOSITIONS CONTAINING THYMOHYDROQUINONE AND THEIR METHOD OF PREPARATION

(71) Applicants: Muhammed Majeed, Edison, NJ (US); Kalyanam Nagabhushanam, East Windsor, NJ (US); Beena Bhat, Bangalore (IN)

(72) Inventors: Muhammed Majeed, Edison, NJ (US); Kalyanam Nagabhushanam, East Windsor, NJ (US); Beena Bhat, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/232,197

(22) Filed: Dec. 26, 2018

(65) Prior Publication Data

US 2019/0192447 A1 Jun. 27, 2019

Related U.S. Application Data

(60) Provisional application No. 62/610,565, filed on Dec. 27, 2017.

(51) Int. Cl.

| | | |
|---|---|---|
| *A61K 31/05* | (2006.01) | |
| *A61K 36/71* | (2006.01) | |
| *A61K 47/22* | (2006.01) | |
| *A61K 47/14* | (2017.01) | |
| *A61K 31/191* | (2006.01) | |
| *A61K 31/704* | (2006.01) | |
| *B01D 11/02* | (2006.01) | |
| *A61K 31/122* | (2006.01) | |
| *A61K 47/12* | (2006.01) | |
| *A61P 39/06* | (2006.01) | |
| *A61P 3/10* | (2006.01) | |
| *A61P 29/00* | (2006.01) | |
| *A61K 31/065* | (2006.01) | |
| *A61K 31/19* | (2006.01) | |

(52) U.S. Cl.
CPC ............ *A61K 31/05* (2013.01); *A61K 31/065* (2013.01); *A61K 31/122* (2013.01); *A61K 31/19* (2013.01); *A61K 31/191* (2013.01); *A61K 31/704* (2013.01); *A61K 36/71* (2013.01); *A61K 47/12* (2013.01); *A61K 47/14* (2013.01); *A61K 47/22* (2013.01); *A61P 3/10* (2018.01); *A61P 29/00* (2018.01); *A61P 39/06* (2018.01); *B01D 11/0203* (2013.01); *B01D 11/0288* (2013.01); *A61K 2236/00* (2013.01); *B01D 11/0211* (2013.01); *B01D 11/0292* (2013.01)

(58) Field of Classification Search
CPC .......... A61K 31/05; A61P 39/06; A61P 29/00
See application file for complete search history.

(56) References Cited

PUBLICATIONS

Awad (Aquaculture; 388-391 (2013) 193-197).*
Amin (Planta Medica; 2016; 82; 8-16).*

* cited by examiner

*Primary Examiner* — Pancham Bakshi

(57) ABSTRACT

Disclosed are compositions enriched with thymohydroquinone, further comprising of thymoquinone, hederagenin and/or α-hederin formulated by blending the active molecules isolated from the seeds of *Nigella sativa*. Also disclosed are novel processes for the isolation of bioactive components thymohydroquinone, thymoquinone from the seeds of *Nigella sativa*. A process for the isolation α-hederin and hederagenin from the spent material of *Nigella sativa* is also disclosed herein.

3 Claims, 4 Drawing Sheets

COMPOSITIONS CONTAINING THYMOHYDROQUINONE AND THEIR METHOD OF PREPARATION

CROSS-REFERENCE TO RELATED PATENT APPLICATIONS

This application is a non-provisional filing claiming priority from US provisional application no. U.S. 62/610,565, filed on 27 Dec. 2017.

BACKGROUND OF THE INVENTION

Field of the Invention

The present invention in general relates to compositions containing thymohydroquinone. More specifically, the present invention relates to a process for the isolation of thymohydroquinone and other actives from *Nigella sativa*.

Description of Prior Art

*Nigella sativa* is a well known medical plant that is widely used in the Ayurveda, Unani and Siddha systems of medicine. The plant contains many active ingredients which are reported to exhibit therapeutic properties. Some of active ingredients include thymoquinone, thymohydroquinone, dithymoquinone, p-cymene, carvacrol, 4-terpineol, t-anethol, sesquiterpene longifolene, α-pinene, thymol, α hederin and hederagenin (Ahmad et al., A review on therapeutic potential of *Nigella sativa*: A miracle herb, Asian Pac J Trop Biomed. 2013; 3(5): 337-352).

There have been different processes reported for the isolation of bioactives from *Nigella sativa*:
1. Salea et al., Supercritical fluid carbon dioxide extraction of *Nigella sativa* (black cumin) seeds using taguchi method and full factorial design, Biochemical Compounds 2013, doi: 10.7243/2052-9341-1-1.
2. Venkatachallam et al., Chemical composition of *Nigella sativa* L. seed extracts obtained by supercritical carbon dioxide, J Food Sci Technol, 2010; 47(6):598-605.
3. Baharetha et al., Use of *Nigella sativa* Linn. Supercritical Carbon Dioxide Extract for Targeting the Angiogenesis Cascade, Med Aromat Plants 2016, 5(3) 1-12.
4. Baharetha et al., Proapoptotic and Antimetastatic Properties of Supercritical CO2 Extract of *Nigella sativa* Linn. Against Breast Cancer Cells, J Med Food, 2013; 16(12): 20131121-1130.

But the processes are either expensive, time consuming or industrially non-viable with low yield of bioactives. Hence, there exists a technical need for a novel process that is both economical, industrially viable with high yield of the isolated bioactives. The present invention solves the said problem by disclosing a novel, high yielding processes for the isolation of bioactives from *Nigella sativa*.

It is the principle objective of the present invention to disclose a non-obvious and industrially applicable process for the isolation of bioactives from *Nigella sativa*.

It is another objective of the present invention to disclose a composition comprising thymohydroquinone isolated from the seeds of *Nigella sativa*

The present invention fulfils aforesaid objectives and provides further related advantages.

SUMMARY OF THE INVENTION

The invention discloses compositions enriched with thymohydroquinone, further comprising of thymoquinone, α-hederin and/or hederagenin formulated by blending the active molecules isolated from the seeds of *Nigella sativa*. The invention also discloses novel processes for the isolation of bioactive components thymohydroquinone and thymoquinone from *Nigella sativa* using supercritical fluid extraction (SCFE). A process for the isolation of α-hederin and hederagenin from the spent material of *Nigella sativa* is also disclosed herein.

Other features and advantages of the present invention will become apparent from the following more detailed description, which illustrate, by way of example, the principle of the invention.

DESCRIPTION OF PREFERRED EMBODIMENTS

Figure 1:
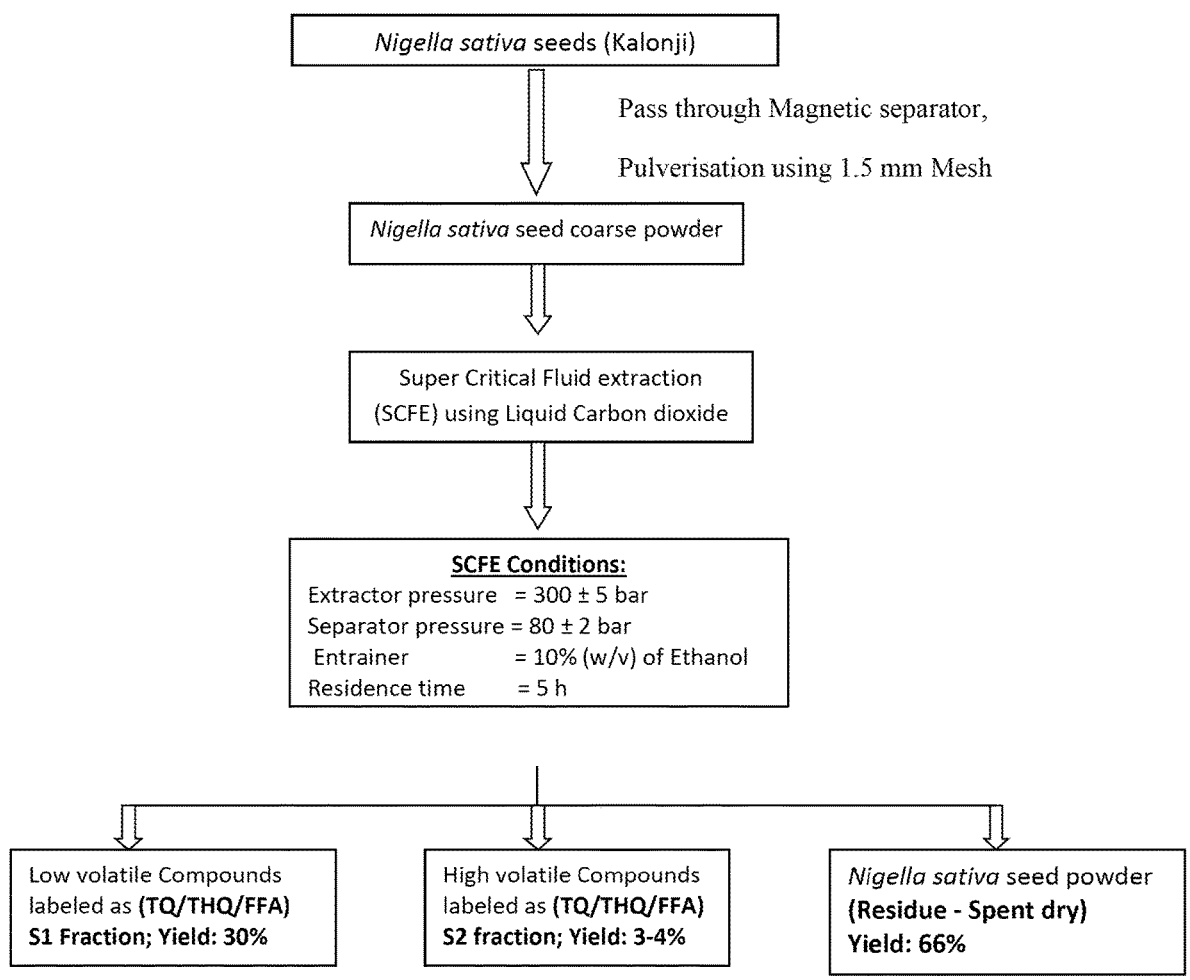
FIG. 1 is a flow chart describing the process for isolating thymoquinone (TQ) and thymohydroquinone (THQ).

In a most preferred embodiment, the present invention discloses a composition comprising thymohydroquinone as represented by STR#1 isolated from the seeds of *Nigella sativa*, wherein said composition is prepared using a process comprising steps of:
a) Powdering the seeds of *Nigella sativa*, pulverizing using 1.5 mm mesh and passing through magnetic separator to obtain a coarse powder;
b) Subjecting the powder of step a) to super critical fluid extraction (SCFE) using liquid CO2 to obtain three fractions: low volatile compounds—S1 fraction, high volatile compounds—S2 fraction and spent residue;
c) Identifying the compounds in low volatile and high volatile fractions as thymoquinone as represented by STR#2, thymohydroquinone as represented by STR#1 and free fatty acids using Gas Chromatography with total yield of about 10-40% in S1 fraction and about 1-6% in S2 fraction respectively;
d) Extracting the spent residue of step b) with 5 volumes of ethanol at 60°–65° C. with stirring for 3 hours;
e) Filtering the concentrating the ethanol extract of step d) to obtain a brownish paste;
f) Dissolving the brownish paste of step e) in water and partitioning thrice with 3 volumes of hexane to obtain aqueous and hexane fractions;
g) Partitioning the aqueous fraction of step f) thrice with n-butanol;
h) Quenching the n-butanol fraction of step g) with water to strip off the solvent while maintaining 20-30% of total dissolved solids;
i) Spray drying to obtain pale brownish powder identified as α-hederin (CAS no. 27013-91-8) represented by STR#3 by HPLC with yield of 0.001-5% on a dry basis;
j) Blending the S2 fraction of step c) with α-hederin of step i) to obtain a mixture comprising thymohydroquinone, thymoquinone, α-hederin and free fatty acids;
k) Dissolving the mixture of step j) with ethanol in a reactor with stirring at 65°–70° C. for 30 minutes to obtain a homogenous mixture;

l) Stripping off the ethanol from mixture of step k) under vacuum and filtering to remove insolubles to obtain a brownish yellow oily liquid;
m) Adding stabilizing agents and bioavailability enhances to the mixture of step l)
n) Formulating the mixture of step m) into tablets, capsules, soft gels, powder, pills, syrups, lozenges, suspension, emulsions.

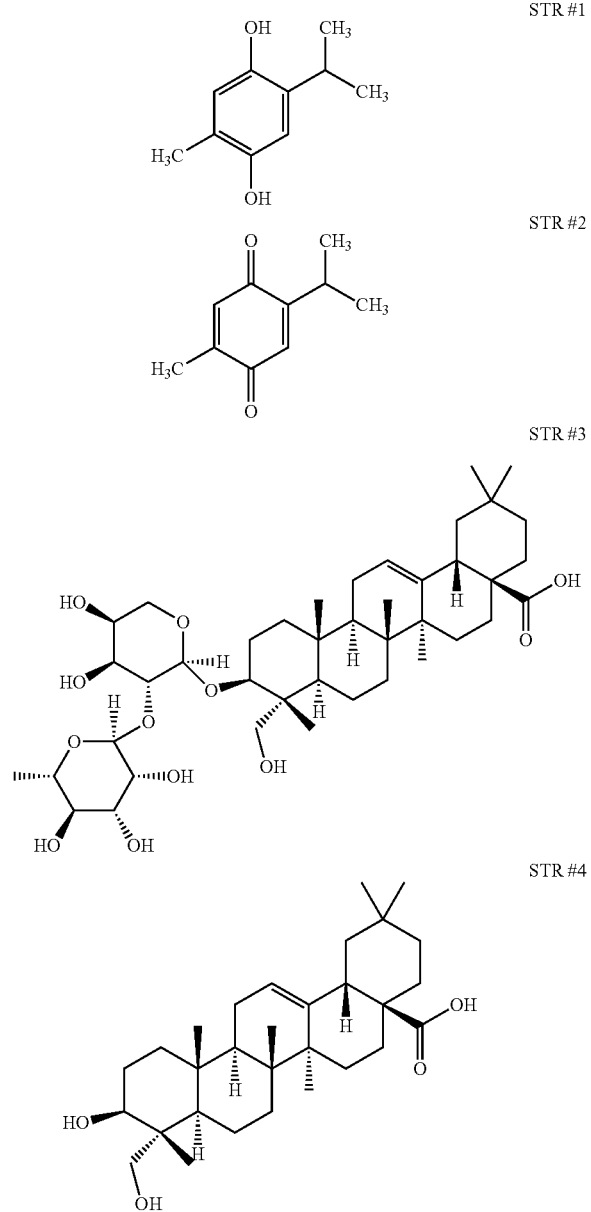

In a related embodiment, the composition is standardised to contain about 0.1%-5% w/w thymoquinone, about 0.01%-10% w/w thymohydroquinone, about 20%-95% w/w fatty acids, about 0.001%-3% w/w α-hederin, 0.1%-4.0% w/w stabilizing agent and 0.2%-2% w/w bioavailability enhancer. In another related embodiment, the free fatty acids in the compositions comprises of than 0.5% w/w Ω 3 (omega 3) fatty acids, 40%-70% w/w Ω 6 (omega 6) fatty acids and 15%-25% w/w Ω 9 (omega 9) fatty acids. In another related embodiment, the stabilizing agent is selected from the group consisting of rosmarinic acid, butylated hydroxyanisole, butylated hydroxytoluene, sodium metabisulfite, propyl gallate, cysteine, ascorbic acid and tocopherols. In a related embodiment, the stabilizing agent is preferably rosmarinic acid. In yet another related embodiment the bioavailability enhancer is selected from the group of piperine, quercetin, garlic extract, ginger extract, and naringin. In a related embodiment, the bioavailability enhancer is preferably piperine.

In another preferred embodiment, the present invention discloses a composition comprising thymohydroquinone as represented by STR#1 isolated from the seeds of *Nigella sativa*, wherein said composition is prepared using a process comprising steps of:
  a) Powdering the seeds of *Nigella sativa*, pulverizing using 1.5 mm mesh and passing through magnetic separator to obtain a coarse powder;
  b) Subjecting the powder of step a) to super critical fluid extraction (SCFE) using liquid CO2 to obtain three fractions: low volatile compounds—S1 fraction, high volatile compounds—S2 fraction and spent residue;
  c) Identifying the compounds in S1 fraction and S2 fraction as thymoquinone as represented by STR#2, thymohydroquinone as represented by STR#1 and free fatty acids using Gas Chromatography with total yield of about 10-40% in S1 fraction and about 1-6% in S2 fraction respectively;
  d) Extracting the spent residue of step b) with 5 volumes of ethanol at 60°-65° C. with stirring for 3 hours;
  e) Filtering the concentrating the ethanol extract of step d) to obtain a brownish paste;
  f) Dissolving the brownish paste of step e) in water and partitioning thrice with 3 volumes of hexane to obtain aqueous and hexane fractions;
  g) Partitioning the aqueous fraction of step f) thrice with n-butanol;
  h) Quenching the n-butanol fraction of step g) with Water to strip off the solvent while maintaining 20-30% of total dissolved solids;
  i) Spray drying to obtain pale brownish powder identified as α-hederin represented by STR#3 by HPLC with yield of 0.001-5% on a dry basis;
  j) Subjecting the powder of step i) to mild hydrolysis by dissolving in 2 volumes of ethanol, 1.4 volumes of 2N HCl and heating the mixture at 50°-60° C. with stirring for 5-6 hours;
  k) Striping off the Ethanol fraction from Reaction mass to obtain Ethyl acetate fraction;
  l) Washing the ethyl acetate fraction with 2% Na2CO3 solution to neutralise the pH;
  m) Separating the ethyl acetate fraction and concentrating to obtain a pale brown powder identified by HPLC as hederagenin represented by STR#4 with assay 40-70%;
  n) Blending the S2 fraction of step c) with hederagenin of step m) to obtain a mixture comprising thymohydroquinone, thymoquinone, hederagenin and free fatty acids;
  o) Dissolving the mixture of step n) with ethanol in a reactor with stirring at 65°-70° C. for 30 minutes to obtain a homogenous mixture;
  p) Stripping off the ethanol from mixture of step o) under vacuum and filtering to remove insolubles to obtain a brownish yellow oily liquid;
  q) Adding stabilizing agents and bioavailability enhances to the mixture of step p)

r) Formulating the mixture of step q) into tablets, capsules, soft gels, powder, pills, syrups, lozenges, suspension, emulsions.

In a related embodiment, the composition is standardised to contain about 0.1%-5% w/w thymoquinone, about 0.01%-10% w/w thymohydroquinone, about 20%-95% w/w fatty acids, about 0.001%-3% w/w hederagenin, 0.1%-4.0% w/w stabilizing agent and 0.2%-2% w/w bioavailability enhancer. In another related embodiment, the free fatty acids in the compositions comprises of less than 0.5% w/w Ω 3 (omega 3) fatty acids, 40%-70% w/w Ω 6 (omega 6) fatty acids and 15%-25% w/w Ω 9 (omega 9) fatty acids. In another related embodiment, the stabilizing agent is selected from the group consisting of rosmarinic acid, butylated hydroxyanisole, butylated hydroxytoluene, sodium metabisulfite, propyl gallate, cysteine, ascorbic acid and tocopherols. In a related embodiment, the stabilizing agent is preferably rosmarinic acid. In yet another related embodiment the bioavailability enhancer is selected from the group of piperine, quercetin, garlic extract, ginger extract, and naringin. In a related embodiment, the bioavailability enhancer is preferably piperine.

In yet another preferred embodiment, the present invention discloses a composition comprising thymohydroquinone as represented by STR#1 isolated from the seeds of Nigella sativa, wherein said composition is prepared using a process comprising steps of:
a) Powdering the seeds of Nigella sativa, pulverizing using 1.5 mm mesh and passing through magnetic separator to obtain a coarse powder;
b) Subjecting the powder of step a) to super critical fluid extraction (SCFE) using liquid CO2 to obtain three fractions: low volatile compounds—S1 fraction, high volatile compounds—S2 fraction and spent residue;
c) Identifying the compounds in low volatile and high volatile fractions as thymoquinone as represented by STR#2, thymohydroquinone as represented by STR#1 and free fatty acids using Gas Chromatography with total yield of about 10-40% in S1 fraction and about 1-6% in S2 fraction respectively;
d) Extracting the powder of step a) with ethanol to obtain ethanol extract and spent material
e) Drying the spent material of step d) under over at 60° C.-70° C., pulverizing and shifting with 40# mesh to obtain a deoiled powder of Nigella sativa;
f) Blending 2%-5% of S2 fraction obtained from step b) with 30%-40% of ethanol extract of step d) and 50%-70% of deoiled powder from step e) to obtain a composition comprising thymohydroquinone, thymoquinone and free fatty acids;
g) Mixing the composition of step f) with 0.001%-1% of hederagenin, as represented by STR#4, obtained from step m) and/or 0.001%-1% of α-hederin, as represented by STR#3, obtained from step i) of the process mentioned in the second embodiment to obtain a composition comprising thymohydroquinone, thymoquinone, free fatty acids, α-hederin and/or hederagenin;
h) Adding stabilizing agents and bioavailability enhances to the composition of step g)
i) Formulating the mixture of step h) into tablets, capsules, soft gels, powder, pills, syrups, lozenges, suspension, emulsions.

In a related embodiment, the composition is standardised to contain about 0.1%-5% w/w thymoquinone, about 0.01%-10% w/w thymohydroquinone, about 20%-95% w/w fatty acids, about 0.001%-3% w/w α-hederin and/or hederagenin, 0.1%-4.0% w/w stabilizing agent and 0.2%-2% w/w bioavailability enhancer. In another related embodiment, the free fatty acids in the compositions comprises of than 0.5% w/w Ω 3 (omega 3) fatty acids, 40%-70% w/w Ω 6 (omega 6) fatty acids and 15%-25% w/w Ω 9 (omega 9) fatty acids. In another related embodiment, the stabilizing agent is selected from the group consisting rosmarinic acid, butylated hydroxyanisole, butylated hydroxytoluene, sodium metabisulfite, propyl gallate, cysteine, ascorbic acid and tocopherols. In a related embodiment, the stabilizing agent is preferably rosmarinic acid. In yet another related embodiment the bioavailability enhancer is selected from the group of piperine, quercetin, garlic extract, ginger extract, and naringin. In a related embodiment, the bioavailability enhancer is preferably piperine.

The aforesaid most preferred embodiments incorporating the technical features and technical effects of instant invention, are explained through illustrative examples herein under.

Example 1: Process for Isolating the Active Molecules from Nigella sativa by SCFE Extraction and Preparing a Formulation The present invention relates to compositions comprising thymohydroquinone and other bioactives isolated from the seeds of Nigella sativa. Flow chart No. 1 (FIG. 1) provides a process for the isolation of thymoquinone (TQ) and thymohydroquinone from the seeds of Nigella sativa:

The process shown in FIG. 1, results in two fractions containing TQ, THQ and free fatty acids with high total yields of 30% and 3-4% respectively. The content of TQ, THQ is proportionately high in the S2 fraction.

Figure 2:
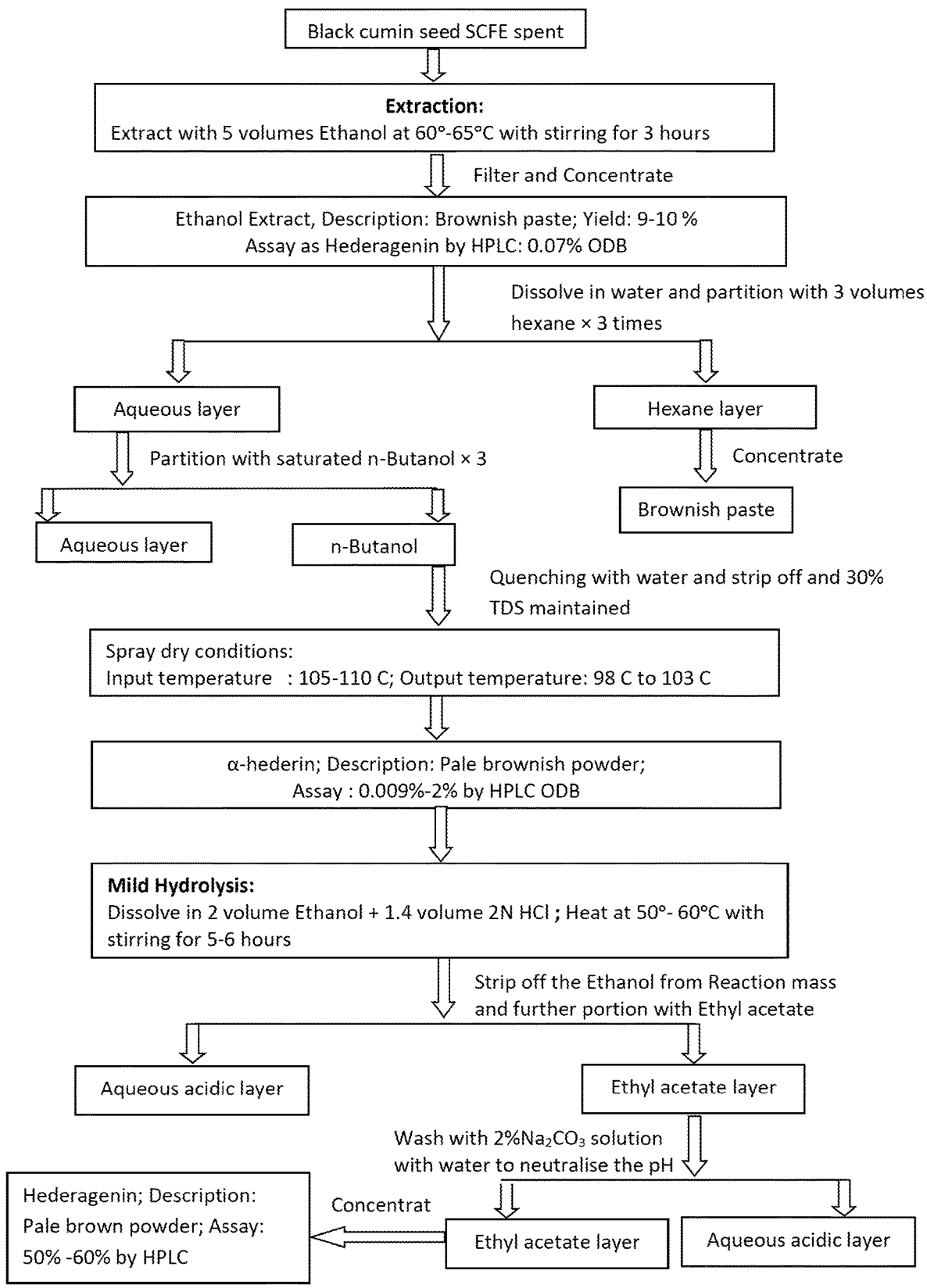
FIG. 2 is a flow chart describing the process for isolating Hederagenin and α-hederin.

The spent material from the above process was processed to obtain further components like hederagenin and α-hederin. Flow Chart No. 2 (FIG. 2) provides the process for the isolation of hederagenin and α-hederin.

Figure 3:
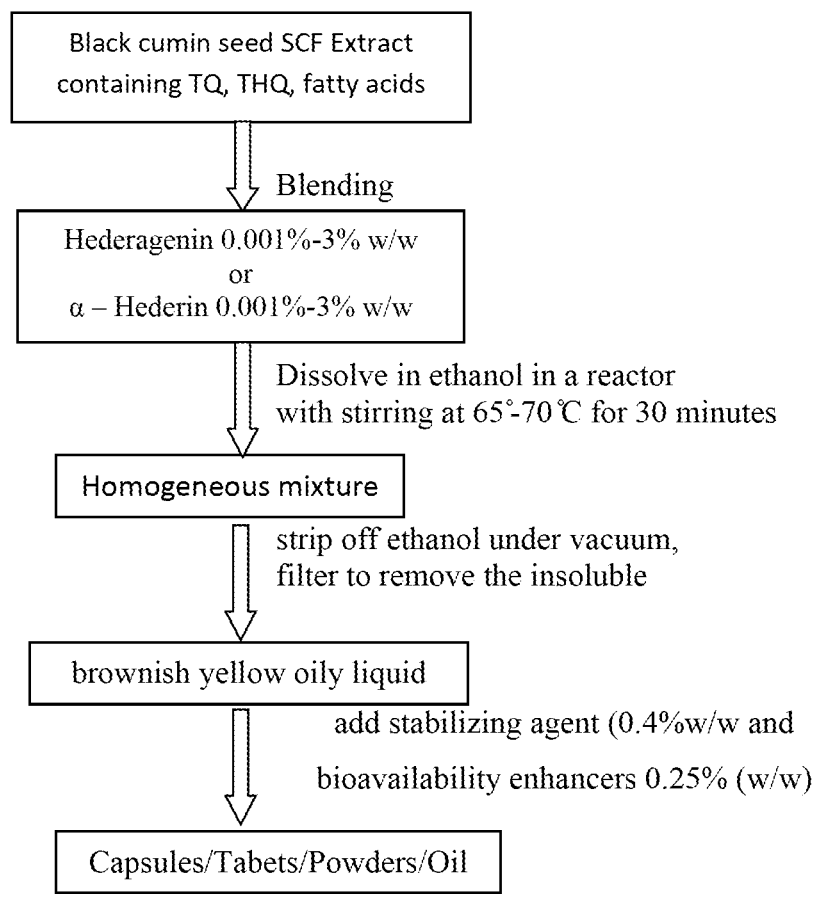
FIG. 3 is a flow chart describing the process for blending a formulation containing thymoquinone, thymohydroquinone, α-hederin or hederagenin.

Flow chart as shown in FIG. 3, describes the process for blending a formulation containing thymoquinone, thymohydroquinone, α-hederin or hederagenin.

Figure 4:
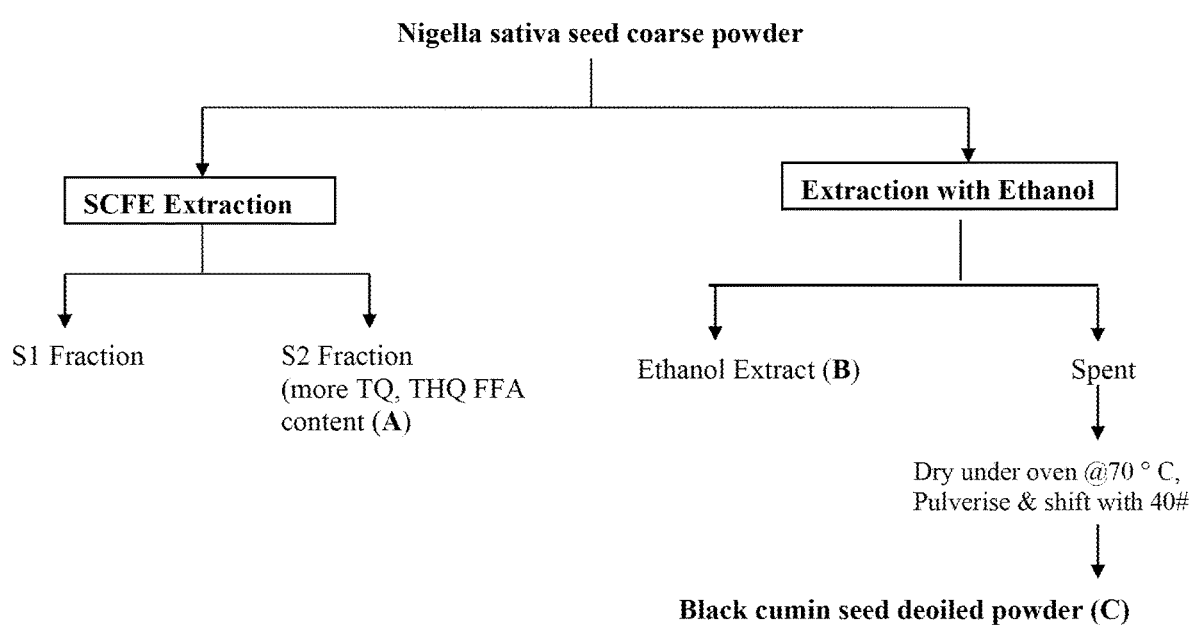
FIG. 4 is a flow chart describing the process of isolation of bioactives from *Nigella sativa*.

Example 2: Process for Isolating the Active Molecules from Nigella sativa by Ethanol Extraction and Preparing a Formulation In an alternate process, the seed of Nigella sativa was subjected to ethanol extraction and the composition was formulated with the bioactives isolated from both SCFE and ethanol extraction. Flow chart No. 4 (FIG. 4) describes the process of isolation of bioactives from Nigella sativa.

A composition containing thymoquinone, thymohydroquinone, α-hederin or hederagenin and free fatty acids was blended from the actives isolated from the above process as described in Table 1.

TABLE 1

Formulation details

| S. No | Name of the material for blending | Name of the Label | Percent Composition (%) |
|---|---|---|---|
| 1 | Black cumin seed SCF extract (S2 Fraction) | A | 2-5 |
| 2 | Black cumin seed ethanol extract | B | 30-40 |
| 3 | Deoiled powder | C | 50-70 |
| 4 | Hederagenin or α-hederin | — | 0.001-1 |

Example 3: Compositions Containing Thymohydroquinone

From the processes described herein above, the following compositions containing thymoquinone, thymohydroquinone, Hederagenin or α-hederin and free fatty acids were formulated. Table 2 describes the different compositions and the concentrations of the individual actives. The compositions further contain stabilizing agents (Rosmarinic acid) and bioavailability enhancers (Piperine).

TABLE 2

Compositions containing thymohydroquinone

| | TQ (%) | THQ (%) | Hederagenin or α-hederin (%) | Fatty acids (%) |
|---|---|---|---|---|
| Composition 1 | 0.1-5.0 | 0.01-10 | 0.001-1 | >85% |
| Composition 2 (White excipient) | 0.1-5.0 | 0.01-10 | 0.001-1 | >20% |
| Composition 3 (Ethanol extraction-Black excipient) | 0.1-5.0 | 0.01-10 | 0.001-1 | >20% |

The total fatty acids in the composition were further characterized using Gas chromatography and were observed to be rich in Ω 3, 6, 9. The results are tabulated in table 3:

TABLE 3

Fatty acids in the compositions containing thymohydroquinone

| Name of the Fatty acid | Composition 1 (%) | Composition 2 (%) | Composition 3 (%) |
|---|---|---|---|
| Omega 3 | 0-0.2 | 0.2 | 0.0 |
| Omega 6 | 50-66 | 55 | 44 |
| Omega 9 | 16-23 | 22 | 18 |

It is well known in the scientific art that thymoquinone and thymohydroquinone are the two main components of black seed essential oil. Although thymohydroquinone is the reduced form of thymoquinone, the chemistry and biological potential of the molecules differ from each other. Studies on the antioxidant and anti-inflammatory potential of the actives indicated that thymohydroquinone is a more potent antioxidant and anti-inflammatory molecule than thymoquinone. Most of the processes that are employed to isolate the bioactive from black seed are enriched with only thymoquinone. The present invention reports a novel process that results in a composition with increased thymohydroquinone content.

Accelerated stability study indicated that there is gradual increase in thymohydroquinone quantity with decrease in content of thymoquinone.

TABLE 4

Accelerated stability study

| Period of study | TQ content by GC (%) | Difference in TQ content | Percentage difference in TQ | THQ content by GC (%) | Difference in THQ content (%) | Percentage difference in THQ |
|---|---|---|---|---|---|---|
| Initial (0 month) | 0.733 | 0 | 0 | 0.033 | 0 | 0 |
| 1st month | 0.717 | 0.016 | −2.18 | 0.037 | 0.004 | +12.12 |
| 2nd month | 0.706 | 0.027 | −3.68 | 0.041 | 0.008 | +24.24 |
| 3rd month | 0.622 | 0.111 | −15.14 | 0.092 | 0.059 | +178.78 |
| 6th month | 0.548 | 0.185 | −25.23 | 0.120 | 0.087 | +263.63 |

Accelerated stability study shows a gradual increase in thymohydroquinone quantity with decrease in content of thymoquinone.

TABLE 5

Long term stability study

| Period of study | TQ content by GC (%) | Difference in TQ content | Percentage difference in TQ | THQ content by GC (%) | Difference in THQ content | Percentage difference in THQ |
|---|---|---|---|---|---|---|
| Initial (0 Month) | 0.733 | 0 | 0 | 0.033 | 0 | 0 |
| 3rd month | 0.643 | 0.09 | −12.27 | 0.095 | 0.062 | +187.88 |
| 6th month | 0.634 | 0.099 | −13.50 | 0.138 | 0.105 | +318.18 |

Thus, the compositions enriched with thymohydroquinone can exhibit improved therapeutic potential and can be administered for the management of many diseases and disorders.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

We claim:

1. A composition comprising thymohydroquinone as represented by STR#1 isolated from the seeds of *Nigella sativa*, wherein said composition is standardised to contain 2%-5% w/w thymoquinone, 0.01%-10% w/w thymohydroquinone, 20%-95% w/w fatty acids, 0.001%-3% w/w α-hederin, 0.1%-4.0% w/w rosmarinic acid and 0.2%-2% w/w piperine.

2. The composition as in claim 1, wherein the composition is prepared using a process comprising steps of:
    o) Powdering the seeds of *Nigella sativa*, pulverizing using 1.5 mm mesh and passing through magnetic separator to obtain a coarse powder;
    p) Subjecting the powder of step a) to super critical fluid extraction (SCFE) using liquid CO2 to obtain three fractions: low volatile compounds—S1 fraction, high volatile compounds—S2 fraction and spent residue;
    q) Identifying the compounds in low volatile and high volatile fractions as thymoquinone as represented by STR#2, thymohydroquinone as represented by STR#1 and free fatty acids using Gas Chromatography with total yield of about 10-40% in S1 fraction and about 1-6% in S2 fraction respectively;
    r) Extracting the spent residue of step b) with 5 volumes of ethanol at 60°–65° C. with stirring for 3 hours;
    s) Filtering the concentrating the ethanol extract of step d) to obtain a brownish paste;
    t) Dissolving the brownish paste of step e) in water and partitioning thrice with 3 volumes of hexane to obtain aqueous and hexane fractions;
    u) Partitioning the aqueous fraction of step f) thrice with n-butanol;
    v) Quenching the n-butanol fraction of step g) with water to strip off the solvent while maintaining 20-30% of total dissolved solids;
    w) Spray drying to obtain pale brownish powder identified as α-hederin (CAS no. 27013-91-8) represented by STR#3 by HPLC with yield of 0.001-5% on a dry basis;
    x) Blending the S2 fraction of step c) with α-hederin of step i) to obtain a mixture comprising thymohydroquinone, thymoquinone, α-hederin and free fatty acids;
    y) Dissolving the mixture of step j) with ethanol in a reactor with stirring at 65°-70° C. for 30 minutes to obtain a homogenous mixture;
    z) Stripping off the ethanol from mixture of step k) under vacuum and filtering to remove insolubles to obtain a brownish yellow oily liquid;
    aa) Adding stabilizing agents (rosmarinic acid) and bioavailability enhancers—pieprine to the mixture of step l)
    bb) Formulating the mixture of step m) into tablets, capsules, soft gels, powder, pills, syrups, lozenges, suspension, emulsions.

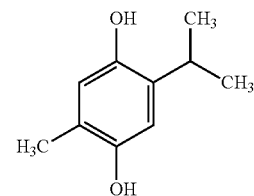

STR #1

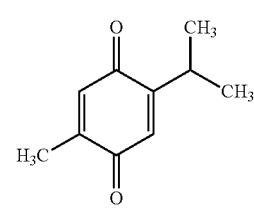

STR #2

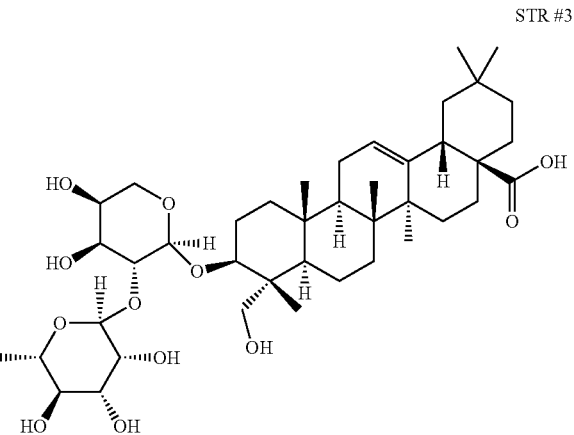

STR #3

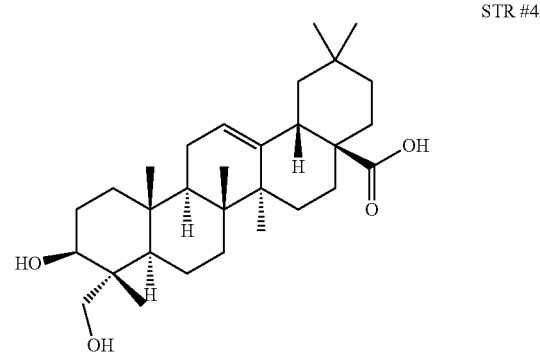

STR #4

3. The composition as in claim 1, wherein the free fatty acids in the compositions comprises of less than 0.5% w/w Ω 3 (omega 3) fatty acids, 40%-70% w/w Ω 6 (omega 6) fatty acids and 15%-25% w/w Ω 9 (omega 9) fatty acids.

* * * * *

UNITED STATES PATENT AND TRADEMARK OFFICE
CERTIFICATE OF CORRECTION

| | |
|---|---|
| PATENT NO. | : 10,945,969 B2 |
| APPLICATION NO. | : 16/232197 |
| DATED | : March 16, 2021 |
| INVENTOR(S) | : Muhammed Majeed, Kalyanam Nagabhushanam and Beena Bhat |

It is certified that error appears in the above-identified patent and that said Letters Patent is hereby corrected as shown below:

In the Claims

Column 9 Lines 19-Column 10 Line 3 Claim 2 should read:
The composition as in claim 1, wherein the composition is prepared using a process comprising steps of:
a) Powdering the seeds of Nigella sativa, pulverizing using 1.5 mm mesh and passing through magnetic separator to obtain a coarse powder;
b) Subjecting the powder of step a) to super critical fluid extraction (SCFE) using liquid $CO_2$ to obtain three fractions: low volatile compounds - S1 fraction, high volatile compounds - S2 fraction and spent residue;
c) Identifying the compounds in low volatile and high volatile fractions as thymoquinone as represented by STR#2, thymohydroquinone as represented by STR#1 and free fatty acids using Gas Chromatography with total yield of about 10-40% in S1 fraction and about 1-6% in S2 fraction respectively;
d) Extracting the spent residue of step b) with 5 volumes of ethanol at 60°-650C with stirring for 3 hours;
e) Filtering the concentrating the ethanol extract of step d) to obtain a brownish paste;
f) Dissolving the brownish paste of step e) in water and partitioning thrice with 3 volumes of hexane to obtain aqueous and hexane fractions;
g) Partitioning the aqueous fraction of step f) thrice with n-butanol;
h) Quenching the n-butanol fraction of step g) with water to strip off the solvent while maintaining 20-30% of total dissolved solids;
i) Spray drying to obtain pale brownish powder identified as α-hederin (CAS no. 27013-91-8) represented by STR#3 by HPLC with yield of 0.001-5% on a dry basis;
j) Blending the S2 fraction of step c) with α-hederin of step i) to obtain a mixture comprising thymohydroquinone, thymoquinone, α-hederin and free fatty acids;
k) Dissolving the mixture of step j) with ethanol in a reactor with stirring at 650-700C for 30 minutes to obtain a homogenous mixture;
l) Stripping off the ethanol from mixture of step k) under vacuum and filtering to remove insolubles to obtain a brownish yellow oily liquid;

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office* m) Adding stabilizing agents (rosmarinic acid) and bioavailability enhancers - piperine to the mixture of step l)

n) Formulating the mixture of step m) into tablets, capsules, soft gels, powder, pills, syrups, lozenges, suspension, emulsions.